(12) United States Patent
Bonny et al.

(10) Patent No.: US 11,653,976 B2
(45) Date of Patent: May 23, 2023

(54) AUTOMATED ARTHROPLASTY PLANNING

(71) Applicant: THINK SURGICAL, INC., Fremont, CA (US)

(72) Inventors: Daniel P. Bonny, Fremont, CA (US); Saurabh Jain, Fremont, CA (US)

(73) Assignee: Think Surgical, Inc., Fremont, CA (US)

( * ) Notice: Subject to any disclaimer, the term of this patent is extended or adjusted under 35 U.S.C. 154(b) by 1187 days.

(21) Appl. No.: 16/080,735

(22) PCT Filed: Mar. 2, 2017

(86) PCT No.: PCT/US2017/020362
§ 371 (c)(1),
(2) Date: Aug. 29, 2018

(87) PCT Pub. No.: WO2017/151863
PCT Pub. Date: Sep. 8, 2017

(65) Prior Publication Data
US 2019/0090952 A1     Mar. 28, 2019

Related U.S. Application Data

(60) Provisional application No. 62/302,770, filed on Mar. 2, 2016.

(51) Int. Cl.
*A61B 34/10*     (2016.01)
*A61B 34/00*     (2016.01)
(Continued)

(52) U.S. Cl.
CPC .............. *A61B 34/10* (2016.02); *A61B 34/25* (2016.02); *G06F 3/04815* (2013.01);
(Continued)

(58) Field of Classification Search
CPC ...................................................... A61B 34/10
(Continued)

(56) References Cited

U.S. PATENT DOCUMENTS 6,033,415 A   3/2000   Mittelstadt et al.
6,430,434 B1  8/2002   Mittelstadt
(Continued)

FOREIGN PATENT DOCUMENTS

JP   2010211464 A   9/2010
JP   2011092405 A   5/2011
(Continued)

OTHER PUBLICATIONS

Office Action issued in corresponding Korean Patent Appln. No. 10-2018-7025712, dated Jun. 23, 2021.
(Continued)

*Primary Examiner* — Javid A Amini
(74) *Attorney, Agent, or Firm* — MaxGoLaw PLLC

(57) ABSTRACT

Systems and methods are provided to aid in planning at least a portion of a total knee arthroplasty procedure. The system and method automatically aligns the implant components and the bones according to a desired clinical alignment goal with minimum user input. The system and method further allows the user to adjust the position and orientation of the femur, tibia, or implant in a clinical direction regardless of a pre-adjusted position and orientation of the femur, tibia, or implant. The graphical user interface is provided that includes a three-dimensional (3-D) view window, a view options window, a patient information window, an implant family window, a workflow-specific tasks window, and a limb and knee alignment measures window.

19 Claims, 9 Drawing Sheets

(51) Int. Cl.
*G16H 50/50* (2018.01)
*G06F 3/04815* (2022.01)

(52) U.S. Cl.
CPC ........ *G16H 50/50* (2018.01); *A61B 2034/102* (2016.02); *A61B 2034/105* (2016.02); *A61B 2034/107* (2016.02); *A61B 2034/108* (2016.02); *A61B 2034/252* (2016.02)

(58) Field of Classification Search
USPC .......................................................... 703/11
See application file for complete search history.

(56) References Cited

U.S. PATENT DOCUMENTS

| | | | |
|---|---|---|---|
| 8,214,016 | B2 | 7/2012 | Lavallee et al. |
| 8,737,700 | B2 * | 5/2014 | Park .................. A61B 5/055 382/128 |
| 8,867,809 | B2 | 10/2014 | Vincent et al. |
| 8,977,021 | B2 * | 3/2015 | Kang .................. A61B 6/032 382/128 |
| 10,779,751 | B2 * | 9/2020 | Macht .................. G06T 3/403 |
| 2002/0045812 | A1 * | 4/2002 | Ben-Haim ............ A61B 5/287 600/407 |
| 2005/0113846 | A1 * | 5/2005 | Carson .................. A61F 2/461 606/130 |
| 2007/0270680 | A1 | 11/2007 | Sheffer et al. |
| 2010/0153081 | A1 | 6/2010 | Bellettre et al. |
| 2011/0196377 | A1 * | 8/2011 | Hodorek ............ A61B 17/155 606/87 |
| 2013/0072821 | A1 * | 3/2013 | Odermatt ................ A61B 5/06 600/595 |
| 2013/0096373 | A1 * | 4/2013 | Chabanas ............ A61B 1/317 600/101 |
| 2013/0144570 | A1 | 6/2013 | Axelson et al. |
| 2014/0188240 | A1 * | 7/2014 | Lang .................... A61F 2/3662 29/592 |
| 2015/0057756 | A1 * | 2/2015 | Lang ................ A61B 17/1675 623/18.11 |
| 2015/0178918 | A1 * | 6/2015 | Arnaud ................ G06T 7/0012 382/131 |
| 2015/0250552 | A1 * | 9/2015 | Radermacher ............ A61F 2/46 703/11 |
| 2015/0250597 | A1 * | 9/2015 | Lang .................... A61F 2/3609 623/22.15 |
| 2015/0265362 | A1 | 9/2015 | Andersson et al. |
| 2015/0324114 | A1 | 11/2015 | Hurley et al. |
| 2016/0038293 | A1 * | 2/2016 | Slamin .................. A61F 2/3859 623/20.35 |
| 2016/0045317 | A1 * | 2/2016 | Lang .................... A61F 2/30942 700/98 |
| 2016/0287395 | A1 * | 10/2016 | Khalili .................. A61F 2/4684 |
| 2017/0164957 | A1 * | 6/2017 | Bojarski ................ A61B 17/17 |
| 2017/0202622 | A1 | 7/2017 | Park et al. |
| 2017/0249440 | A1 * | 8/2017 | Lang ...................... B22F 10/80 |
| 2017/0258526 | A1 * | 9/2017 | Lang ...................... A61B 34/74 |
| 2018/0082480 | A1 * | 3/2018 | White ...................... G06F 3/017 |

FOREIGN PATENT DOCUMENTS

| | | | |
|---|---|---|---|
| JP | 2011518645 A | | 6/2011 |
| JP | 2012224721 A | | 11/2012 |
| JP | 2013503007 A | | 1/2013 |
| JP | 2016504162 A | | 2/2016 |
| WO | 2005087125 A2 | | 9/2005 |
| WO | 2006078236 A1 | | 7/2006 |
| WO | 2007017642 A1 | | 2/2007 |
| WO | 2014045119 A2 | | 3/2014 |
| WO | WO-2016086049 A1 * | 6/2016 | ............ A61B 34/10 |

OTHER PUBLICATIONS

Office Action issued in corresponding Japanese Patent Appln. No. 2018-544828, dated Nov. 29, 2021.
Supplementary Partial European Search Report dated Feb. 14, 2020, issued in corresponding European Appln. No. EP17760777.
Reasons for Rejection for JP2018-544828, dated Dec. 24, 2020.

* cited by examiner

AUTOMATED ARTHROPLASTY PLANNING

CROSS-REFERENCE TO RELATED APPLICATION

This application claims priority of U.S. Provisional Patent Application Ser. No. 62/302,770 filed Mar. 2, 2016, which is incorporated herein by reference.

TECHNICAL FIELD

The present invention generally relates to the field of computer-aided surgical planning, and more specifically to a computerized method to intuitively plan a total knee arthroplasty procedure.

BACKGROUND

Total knee arthroplasty (TKA) is a surgical procedure in which the articulating surfaces of the knee joint are replaced with prosthetic components, or implants. TKA requires the removal of worn or damaged cartilage and bone on the distal femur and proximal tibia. The removed cartilage and bone is then replaced with synthetic implants, typically formed of metal or plastic, to create new joint surfaces.

Computer-assisted surgical systems and patient specific instrumentation (PSI) are gaining popularity as a tool to pre-operatively plan and precisely execute the surgical plan to ensure an accurate final position and alignment of an implant within a knee joint of a patient that can improve long term clinical outcomes and increase the survival rate of the prosthesis. In general, the computer-assisted surgical systems and PSI systems include two components, an interactive pre-operative planning software program and a computer-assisted surgical device or PSI that utilizes the pre-operative data from the software to assist the surgeon in precisely executing the procedure.

Conventional interactive pre-operative planning software generates a three-dimensional (3-D) model of the patient's bony anatomy from a computed tomography (CT) or magnetic resonance imaging (MRI) image data set of the patient. A set of 3-D computer aided design (CAD) models of the manufacturer's implants are pre-loaded in the software that allows the user to place the components of a desired implant to the 3-D model of the bony anatomy to designate the best position and alignment of the implant on the bone. The pre-operative planning data is used to either fabricate the patient specific instrumentation, or it is loaded and read by a surgical device to assist the surgeon intra-operatively in executing the plan. Such data is also of value in positioning a surgical robot so as to insure spatial access of the robot to the needed surgical field while retaining human access to the same.

However, some pre-operative planning software is limited in a few regards that inhibit the ability of a user to intuitively plan all six degrees of freedom of the implants in TKA. First, the user may have to perform a majority of the planning steps manually. For instance, the user identifies a majority of the anatomical landmarks on the femur and the tibia to determine various anatomical references (e.g., the mechanical axis). Second, as the user manually adjusts the position and orientation of the implant, a series of sequential rotations and translations may cause a subsequent or previous degree of freedom to change un-intuitively. This is inherently due to the additive changes in the orientation of the coordinate system of the implant as the implant is sequentially rotated or translated. This is non-intuitive because the user is trying to accomplish certain clinical alignment goals that are measured with respect to three well-established orthogonal planes. Those orthogonal planes include the coronal plane to accomplish a desired clinical varus-valgus, the axial plane to accomplish a desired clinical internal-external, and the sagittal plane to ensure the implant fits properly for a desired varus-valgus and internal-external alignment goal. The clinical alignment goals measured from these planes are important because they are a standard in the industry and are used by surgeons to assess clinical outcomes and implant alignment postoperatively.

Another limitation of the conventional pre-operative planning software is the inability to allow a surgeon or different surgeons to plan for different alignment goals, automatically. Different surgeons have different implant alignment strategies. For example, for varus-valgus alignment, some surgeons prefer to align the implants to restore the mechanical axis of the leg, while others prefer to align the implants to restore the native kinematics of the knee. Likewise, for internal-external alignment, some surgeons prefer to align the implant with the transepicondylar axis, while others prefer a native kinematic alignment. Conventional planning software may be limited to automatically aligning the implant to the bone according to a single default alignment goal strategy. As a result, a desired outcome may be a priori impossible. Additionally, in situations where bone characteristics are abnormal as to a parameter such as density or structure, the ability to re-select alignment strategy can afford considerably better clinical results.

Finally, the conventional planning software does not allow the user to simply input each of their alignment goals and have the system automatically output a transformation between the implant and the bone that can be readily used by a computer-assisted surgical system. If the system was capable of automatically aligning the implant to the bone without any manual user adjustments, it may greatly reduce the time spent creating the pre-operative plan, which saves money for the surgeon and health care facility.

Thus, there is a need for a system and method that automatically aligns an implant to a bone with minimal user input. There is also a need for a pre-operative planning method that allows a user to make an adjustment to the placement of an implant with respect to a bone, in a direction corresponding to a clinical alignment goal or clinical direction, regardless of a pre-adjusted position and orientation of the implant. There is a further need to provide a system and method that automatically aligns an implant to a bone with minimal user input.

SUMMARY OF THE INVENTION

A computerized method is provided for planning an arthroplasty procedure according to a user's clinical alignment goals. The method includes providing a graphical user interface (GUI) and virtual models of the first bone and the second bone involved in the arthroplasty procedure via the GUI, locating a set of anatomical landmarks located on the virtual models of the first bone and the second bone, and automatically determining, by a processor, three orthogonal planes with respect to each of the virtual models of the first bone and the second bone using at least a portion of the anatomical landmarks. The method further includes receiving user selections and re-selection of: an implant from a library of implants, the implant having a first implant for the first bone and a second implant for the second bone, where each implant for the femur and the tibia have an associated virtual model of the implant, and at least one clinical alignment goal from a set of alignment goals. The model of the first bone and the second bone are automatically aligned to the model of the implant to satisfy the at least one alignment goal. The first bones and the second bones are connected and illustratively include the femur-tibia, femur-pelvis, humerus-scapula pairs, respectively.

A surgical planning system is provided for planning an arthroplasty procedure according to a user's clinical alignment goals. The system includes a workstation having a computer, user-peripherals, and a monitor for displaying a graphical user interface (GUI). The computer has a processor, non-transient storage memory, and other hardware, software, data and utilities to execute the method for planning a knee arthroplasty procedure according to a user's clinical alignment goals. The peripherals allow a user to interact with the GUI and include user input mechanisms including at least one of a keyboard, mouse, or a touchscreen capability on the monitor.

BRIEF DESCRIPTION OF THE DRAWINGS

The present invention is further detailed with respect to the following drawings. These figures are not intended to limit the scope of the present invention but rather illustrate certain attribute thereof wherein.

DETAILED DESCRIPTION OF THE INVENTION

The present invention has utility as a method and system for performing the same to aid a user in planning at least a portion of an arthroplasty procedure, such as a total knee arthroplasty. The system and method automatically aligns the implant components and the bones according to a desired clinical alignment goal with minimum user input. The system and method further allows the user to adjust the position and orientation of the bones that in the context of a knee arthroplasty are the femur, tibia, or implant in a clinical direction regardless of a pre-adjusted position and orientation of the femur, tibia, or implant.

The following description of the preferred embodiments of the invention in the context of TKA is not intended to limit the invention to these preferred embodiments, but rather to enable any person skilled in the art to make and use this invention. Reference is made herein to the planning of a total knee arthroplasty but it should be appreciated that embodiments of the present invention may be applied or adapted to the planning of other orthopedic surgical procedures illustratively including total hip arthroplasty, hip resurfacing, unicondylar knee arthroplasty, ankle arthroplasty, shoulder arthroplasty, and other joint replacement procedures.

It is to be understood that in instance where a range of values are provided that the range is intended to encompass not only the end point values of the range but also intermediate values of the range as explicitly being included within the range varying by the last significant figure of the range. By way of example, a recited range from 1 to 4 is intended to include 1-2, 1-3, 2-4, 3-4, and 1-4.

Figure 1:
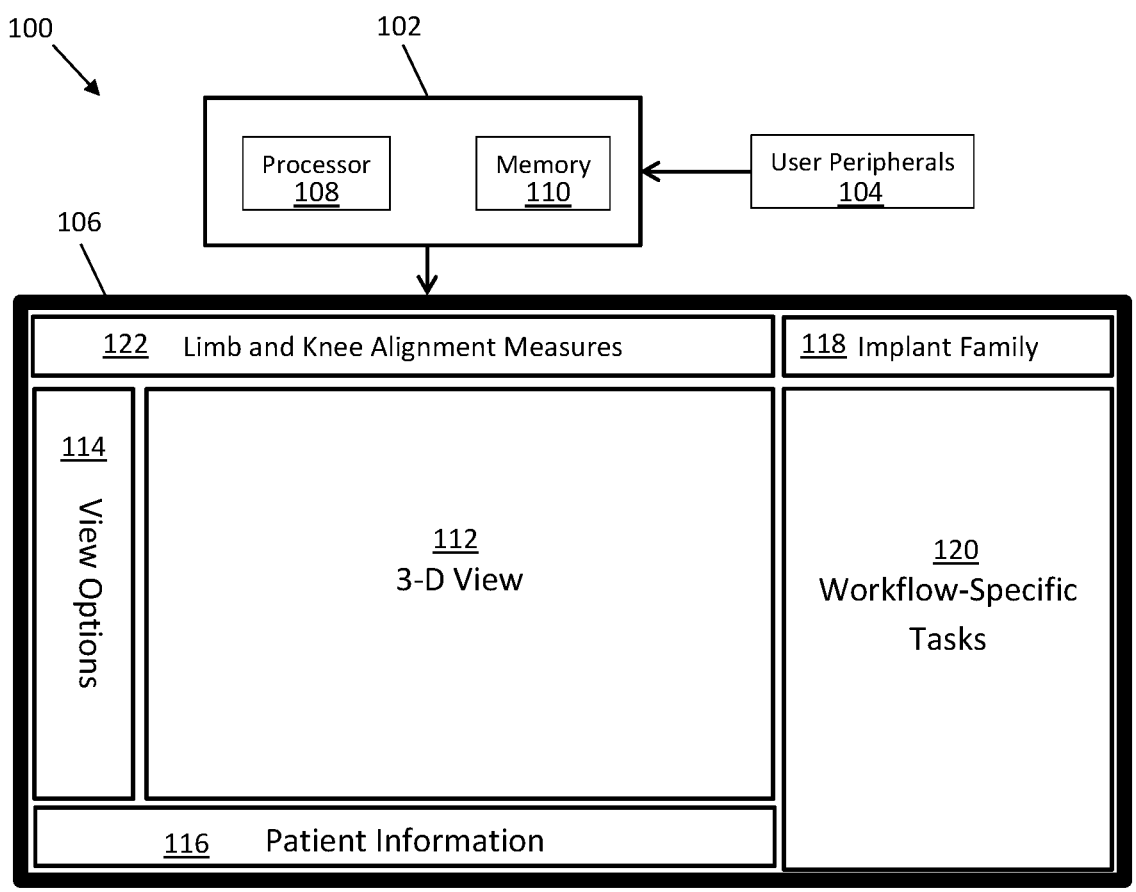
FIG. 1 depicts a high-level overview of a pre-operative planning workstation and graphical user interface in accordance with embodiments of the invention.

With reference to the figures, FIG. 1 illustrates an embodiment of a TKA pre-operative planning workstation 100. The workstation 100 includes a computer 102, user-peripherals 104, and a monitor displaying a graphical user interface (GUI) 106. The computer 102 includes a processor 108, non-transient storage memory 110, and other hardware, software, data and utilities to execute the planning process described herein. The user peripherals 104 allow a user to interact with the GUI 106 and may include user input mechanisms such as a keyboard and mouse, or the monitor may have touchscreen capabilities.

A high-level overview of the GUI 106 is shown in FIG. 1. The GUI 106 includes a three-dimensional (3-D) view window 112, a view options window 114, a patient information window 116, an implant family window 118, a workflow-specific tasks window 120, and a limb and knee alignment measures window 122. Each GUI window can be summarized as follows. The 3-D view window 112 allows the user to view and interact with medical imaging data, 3-D bone models, and 3-D implant component CAD models. The view options window 114 provides widgets to allow the user to quickly change the view of the models of the bone, models of the implant components, and alignment axes, to a desired view. The patient information window 116 displays the patient's information such as name, identification number, gender, surgical procedure, and operating side (e.g., left femur, right femur). The implant family window 118 provides drop-down menus to allow the user to select and re-select a desired implant component from a library of implant components. The workflow-specific tasks window 120 includes various widgets to provide several functions illustratively including: guiding the user throughout different stages of the planning procedure; allowing the user to select and re-select desired alignment goals from a set of alignment goals; allowing the user to adjust the implant component(s) and bone models in desired clinical directions; displaying measured values of the alignment and position of the component(s) on the bone(s); and displaying a summary of the plan. The limb and knee alignment measures 122 displays the alignment and position of the implant components on the bone models such as hip-knee-ankle angle, femoral joint line alignment, and tibial joint line alignment. Overall, the layout of the GUI provides the user with a convenient roadmap and visual display to successfully plan a TKA.

Prior to planning the procedure, imaging data of the patient's femur and tibia are obtained using an imaging modality such as computed tomography (CT), ultrasound, or magnetic resonance imaging (MRI). The imaging data is transferred to the planning workstation 100 typically in a digital imaging and communication in medicine (DICOM) format. Subsequently, a 3-D model of the bone is generated. In a particular embodiment, the patient's bones may be manually, semi-manually, or automatically segmented by a user to generate the 3-D models of the bone. One or more of the bone models can be displayed in the 3-D view window 112, where the user can quickly change to a proximal, distal, medial, lateral, anterior, and posterior view of bone model using corresponding widgets in the view options window 114.

Figure 2A:
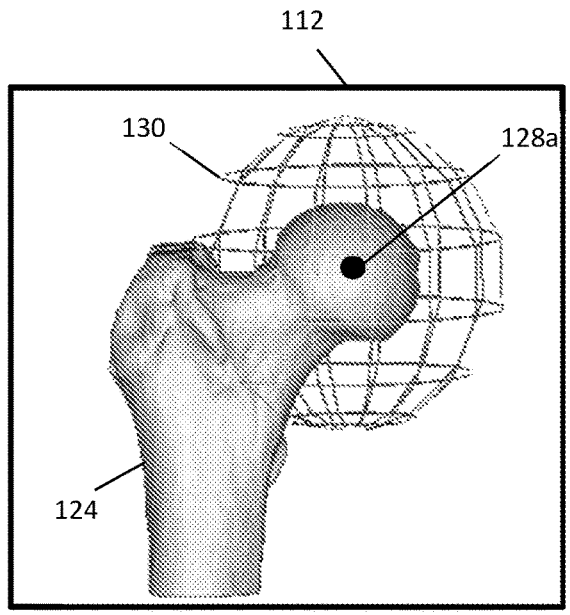
FIGS. 2A-2C illustrate examples of 3-D models of the bone in different views and the locating of anatomical landmarks thereon in accordance with embodiments of the invention.
Figure 2B:
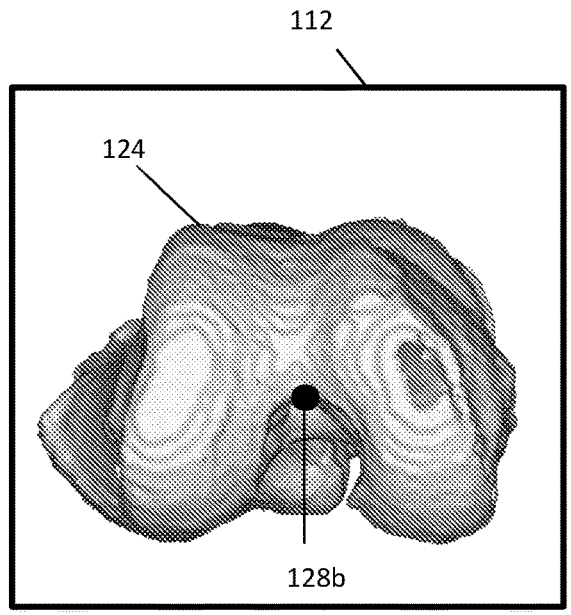
Figure 2C:
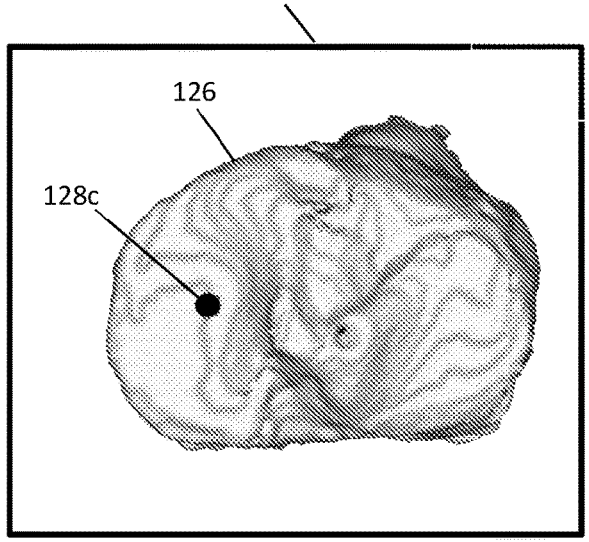

An example of three views of the bone models are shown in FIGS. 2A-2C. A lateral view of femoral bone model 124 is shown in FIG. 2A, a distal view of a femoral bone model 124 is shown in FIG. 2B, and a proximal view of a tibial bone model 126 is shown in FIG. 2C. Anatomical landmarks 128 from a set of anatomical landmarks are located on the femoral model and tibial model to aid in planning. A portion of the anatomical landmarks may also provide the location for registration points to be collected intraoperatively to register the bone models to a computer-assisted surgical system as described in U.S. Pat. No. 6,033,415. The set of anatomical landmarks for the femur may include: the femoral head center 128a, most anterior point in intercondylar notch 128b, medial epicondyle, lateral epicondyle, anterolateral trochlear ridge, anteromedial trochlear ridge, most posterior point on medial condyle, most posterior point on lateral condyle, most distal point on medial condyle, most distal point on lateral condyle, and knee center. The set of anatomical landmarks for the tibia may include: midpoint between tibial splines, ankle center, center of medial plateau 128c, center of lateral plateau, tibia tubercle (medial $\frac{1}{3}^{rd}$), antero-lateral face, and anteromedial face. The processor may identify a portion of the landmarks automatically using an iteration algorithm as described below. The remaining landmarks may be located by the user manually by pointing and clicking on the location of the landmark on the bone models. In a specific embodiment, as the user or computer identifies specific landmarks, those landmarks may be used to provide a specific view (distal, anterior, medial, lateral) of the bone model to easily identify a specific subsequent landmark. For example, after the three clinically standard references planes are automatically determined, the user may choose to identify and locate the center of the knee landmark. The user may click on the prompt, where the view of the bone model automatically shows the distal portion of the knee such the user may quickly locate the center of the knee.

The user may use other landmark locating tools such as a fitting sphere tool 130. A user may adjust the diameter and position of the fitting sphere 130 until the diameter and position approximately matches the diameter and position of a portion of the femoral head. When matched, the center of the fitting sphere 130 defines the femoral head center anatomical landmark 128a. In a specific inventive embodiment, the processor locates all of the landmarks automatically using the statistical model that was used to automatically generate the 3-D models of the bones from the DICOM data. Once the landmarks have been identified, they are accepted by the user and stored.

Figure 3A:
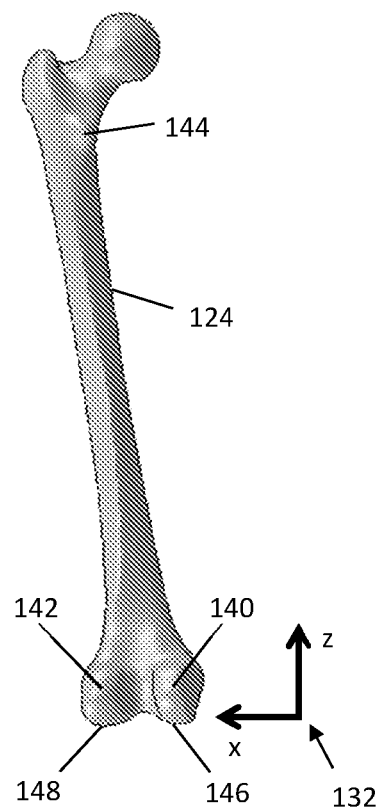
FIGS. 3A-3C depict three orthogonal clinically established reference planes for planning a TKA in accordance with embodiments of the invention.
Figure 3B:
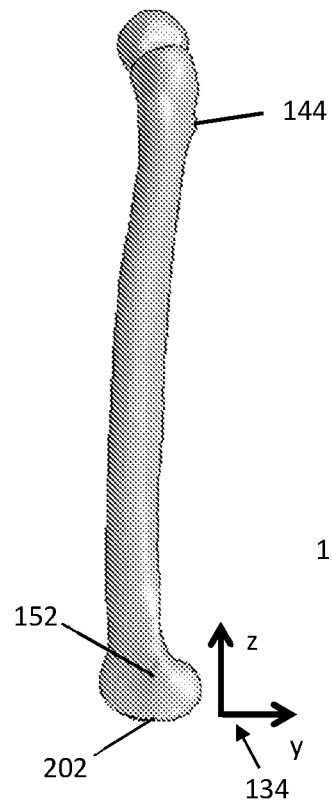
Figure 3C:
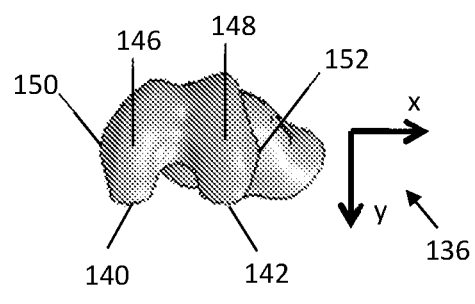

Three orthogonal planes on the femur are determined by the processor, where each plane corresponds to a clinically established standard reference plane for planning any TKA procedure. These planes include a coronal native plane (XZ) 132, a sagittal plane (ZY) 134, and an axial native plane (XY) 136, as shown in FIGS. 3A-3C, respectively. The coronal native plane 132 is defined by the most posterior point on the posterior medial condyle 140, posterior lateral condyle 142, and lesser trochanter 144, such that the plane touches exactly three points but does not intersect the bone. An iterative method to automatically find the coronal native plane 132 includes:

1. Point 1 (lesser trochanter initial guess);
 a. Rotate bone model about axis 1 ($\hat{1}+0\hat{j}+0\hat{k}$ in global LPS (left, posterior, superior) model coordinates);
 b. Find most-posterior (+y) point in global LPS coordinate system; c. Find same point in local coordinates on the bone model;
 d. Rotate bone model about axis 1 back to original orientation;
2. Point 2 (posterior medial/lateral condyle initial guess);
 a. Rotate bone model about axis 2 ($0.577\hat{i}+0.577\hat{j}+0.577\hat{k}$ in global LPS model coordinates);
 b. Find most-posterior (+y) point in global LPS coordinate system; c. Find same point in local coordinates on the bone model;
 d. Rotate bone model about axis 2 back to original orientation;
3. Point 3 (posterior lateral/medial condyle initial guess);
 a. Rotate bone model about axis 3 ($0.577\hat{i}-0.577\hat{j}-0.577\hat{k}$ in global LPS model coordinates);
 b. Find most-posterior (+y) point in global LPS coordinate system;
 c. Find same point in local coordinates on the bone model;
 d. Rotate bone model about axis 3 back to original orientation;
4. Iteratively update points;
 a. Re-orient bone model such that all three points are parallel to the XZ plane;
 b. Find most-posterior (+y) point in global LPS coordinate system;
 c. Find same point in local coordinates on the bone model (Point 4);
 d. Whichever point (point 1, 2, or 3) is closest to Point 4, delete that point and replace it with Point 4;
 e. Repeat a-d until points do not change;

The axial native plane 136 is defined as perpendicular to the coronal native plane on the femur, and coincident with the most distal point on the distal medial condyle 146 and the most distal point on the distal lateral condyle 148. A method to automatically find the axial native plane 136 includes:

1. Point 1 (distal medial/lateral condyle initial guess);
 a. Rotate bone model about axis 1 ($0\hat{i}+1\hat{j}+0\hat{k}$ in global LPS (left, posterior, superior) model coordinates);
 b. Find most-distal (−z) point in global LPS coordinate system;
 c. Find same point in local coordinates on the bone model;
 d. Rotate bone model about axis 1 back to original orientation;
2. Point 2 (posterior medial/lateral condyle initial guess);
 a. Rotate bone model about axis 2 ($0\hat{i}-1\hat{j}+0\hat{k}$ in global LPS model coordinates);
 b. Find most-distal (−z) point in global LPS coordinate system;
 c. Find same point in local coordinates on the bone model;
 d. Rotate bone model about axis 2 back to original orientation;
3. Iteratively update points;
 a. Re-orient bone such that the coronal kinematic plane is coincident with the XZ plane;
 b. Re-orient bone about the Y-axis until both points are parallel with the XY plane;
 c. Find most-distal (−z) point in global coordinate system;
 d. Find same point in local coordinate on the bone model (Point 3);

e. Whichever point (point 1 or 2) is closest to Point 3, delete that point and replace it with Point 3;

f. Re-orient bone such that the bone is in the original coordinate system;

g. Repeat a-f until points do not change.

The sagittal plane 134 is defined as perpendicular to both the coronal native plane 132 and the axial native plane 136, and coincident with a medial-lateral center point of the bone. The medial-lateral center point may be determined by computing the midpoint between the medial epicondyle landmark 150 and the lateral epicondyle landmark 152. These three orthogonal planes are clinically established standard reference planes used for planning any TKA. It should be appreciated that the LPS coordinate system used above is not an essential reference coordinate system to determine the planes (132, 134, 136), where other reference coordinate systems may be used. In addition, the amount to rotate the bone model about the axes 1, 2, and 3 to locate the points that define the planes may be tuned to ensure convergence for different patient positions during scanning.

An initial femur transform is determined using the intersection of the three orthogonal planes to establish a position and orientation of the x, y, and z axes relative to the bone. The initial femur transform provides the basis for aligning and positioning the implant components to the bone models in the clinically established standard reference frame.

Figure 4:
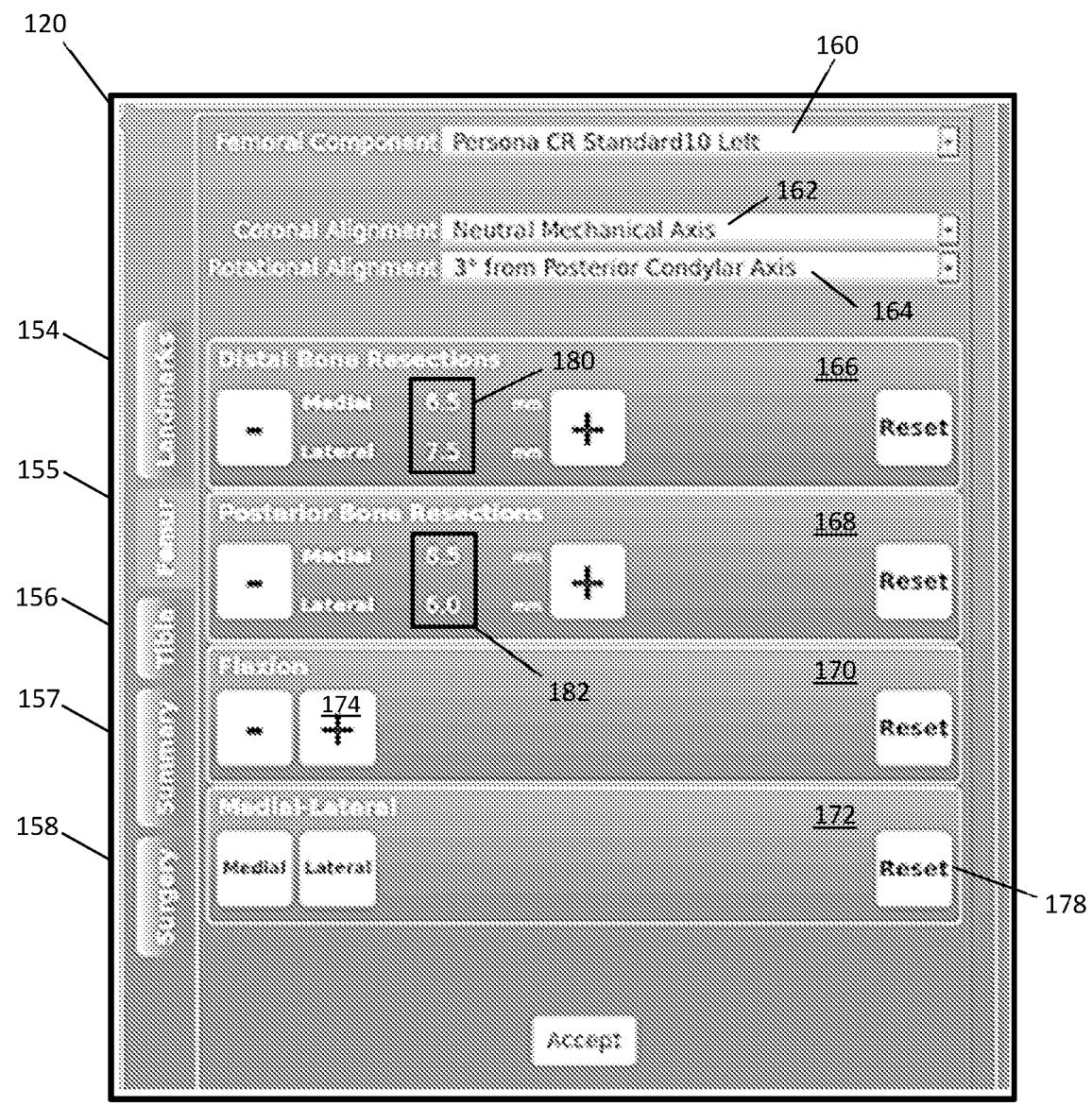
FIG. 4 depicts a femoral planning stage of the GUI in accordance with embodiments of the invention.

With reference to FIG. 4, a workflow-specific tasks window 120 is shown for the femoral planning stage of the planning procedure. Briefly, as shown on the left side of the tasks window 120 are tabs 154-158 which allow the user to toggle between the different planning stages of the procedure (i.e., landmarks stage 154, femur planning stage 155, tibia planning stage 156, summary stage 157, and a surgery planning stage 158). FIG. 4 depicts the tasks window in the femoral planning stage 155. The femoral planning stage includes an implant drop-down menu 160, a coronal alignment goal drop-down menu 162, an axial alignment goal drop-down menu 164, a distal bone resections sub-window 166, a posterior bone resection sub-window 168, a flexion sub-window 170, and a medial-lateral sub-window 172. A user may select and re-select a desired implant from a library of implants using the implant drop-down menu 160. A user may select and re-select a varus-valgus alignment goal from a set of varus-valgus alignment goals using the varus-valgus alignment drop-down menu 162. Likewise, a user may select and re-select an axial rotational alignment goal from a set of axial rotation alignment goals using the axial alignment drop-down menu 164. The set of femoral coronal alignment goals may include a native alignment and a neutral mechanical axis. The set of femoral axial alignment goals may include: parallel to the transepicondylar axis; an angle offset from an anatomical axis (e.g., 1°-10° from the posterior condylar axis); and a native alignment.

Each of the sub-windows 166, 168, 170 and 172, allow the user to adjust the implant or bone in four clinical directions. The four clinical directions include a proximal-distal translational direction (sub-window 166), an anterior-posterior translational direction (sub-window 168), a medial-lateral translational direction (sub-window 172), and a flexion-extension rotational direction (sub-window 170). The directions are referred to as clinical because the user can adjust each direction individually, and an adjustment in the clinical direction corresponds to a direction with reference to the clinically established reference frame, regardless of a pre-adjusted position and orientation of the implant or bone as described below. The user can adjust the clinical direction using the corresponding "+" button 174 or "−" button 176.

Reset buttons 178 allow the user to reset any adjustments to a default value. A measured amount of distal resection on the medial and lateral distal condyles 180 is displayed as the user adjusts any clinical directions and/or selects/reselects an implant or alignment goal. Similarly, a measured amount of posterior bone resection on the medial and lateral posterior condyles 182 is displayed as the user adjusts any clinical directions and/or selects/reselects an implant or alignment goal. In a particular inventive embodiment, an additional sub-window allows the user to adjust for an estimated or measured cartilage thickness, cartilage wear, or bone wear to translate the implant accordingly.

Figure 5A:
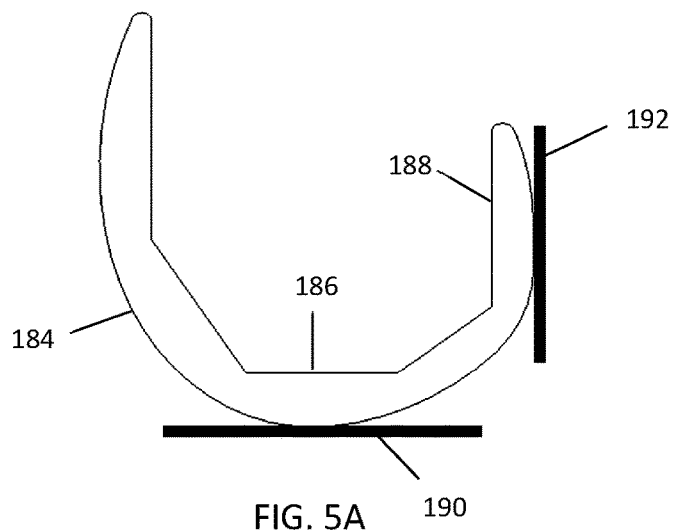
FIGS. 5A-5C depict the alignment of a femoral component on a model of a femur in accordance with embodiments of the invention.
Figure 5B:
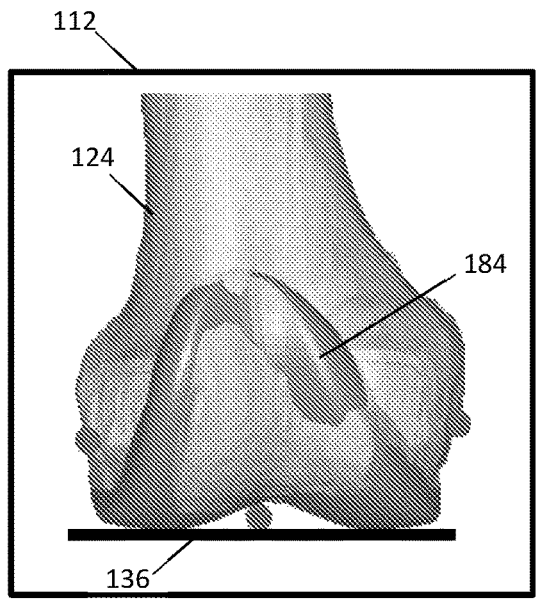
Figure 5C:
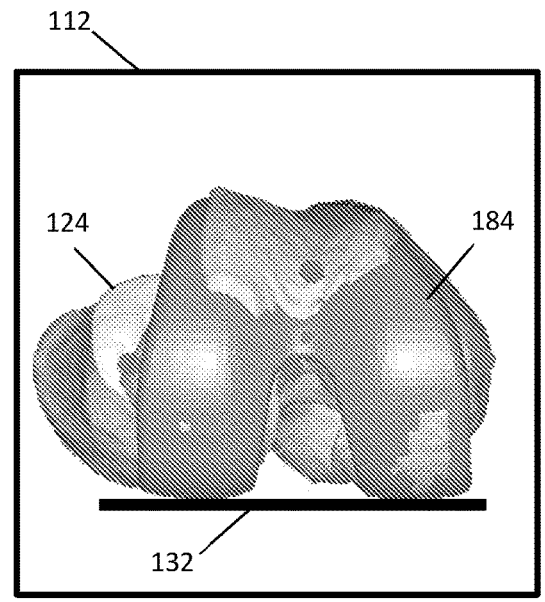

A default femoral coronal alignment goal, and femoral axial alignment goal are pre-set when the user enters to the femur planning stage. A user then selects a femoral implant component, and the femoral bone model is automatically aligned to the selected implant according to the default alignment goal. The default alignment goals may be a native femoral coronal alignment and a native femoral axial alignment. The processor automatically aligns the bone to the implant using the initial femur transform, the native alignment goals, and a portion of the geometry of the implant. An example of a femoral implant component 184 is shown in FIG. 5A. The femoral implant 184 includes a distal planar surface 186 to interact with a distal bone cut and a posterior planar surface 188 to interact with the posterior bone cut. The planar surfaces (186, 188) are also referred to herein as implant cut planes. A femoral implant distal articular plane 190 is defined as an offset plane from the distal planar surface 186 by a maximum thickness of the distal portion of the implant. Likewise, a femoral implant posterior articular plane 192 is defined as an offset plane from the posterior planar surface 192 by a maximum thickness of the posterior portion of the implant. The articular planes (190, 192) are also referred to herein as offset implant cut planes. The processor then automatically aligns the implant to a native alignment goal by aligning the axial native plane 136 to the implant distal articular plane 190, and the coronal native plane 132 to the implant posterior articular plane 192. FIGS. 5B and 5C display the result of the femur model 124 and the implant 184 aligned in native alignment.

When a user selects a mechanical axis coronal alignment and a non-native axial alignment for the femur, projection angles rather than direction cosines are used to build a rotational adjustment transform to align the implant and the bone. By using projection angles, individual degrees of freedom can be changed/adjusted without substantially affecting the other degrees of freedom and subsequent changes/adjustments do not substantially affect previous adjustments/changes. In one inventive embodiment, substantially affecting the other degrees of freedom refers to 1 mm or 1 degree. In another inventive embodiment, the substantially affecting refers to 0.5 mm and 0.5 degrees. While in other inventive embodiments, the substantially affecting refers to 0.1 mm and 0.1 degrees.

For example, when a user selects a mechanical axis alignment, the mechanical axis (defined as an axis connecting the femoral head center and the center of the knee) is projected onto the coronal native plane 132. The angle between the z-axis and the projected mechanical axis is determined and used to build a portion of the rotational adjustment transform. Simultaneously, when a user selects, for example, the transepicondylar axis (defined as an axis connecting the medial and lateral epicondyles) is projected onto the axial native plane 136. The angle between the x-axis and projected transepicondylar axis is determined to build the second portion of the rotation adjustment transform. The user can make any adjustments in the other clinical directions as desired.

Figure 6A:
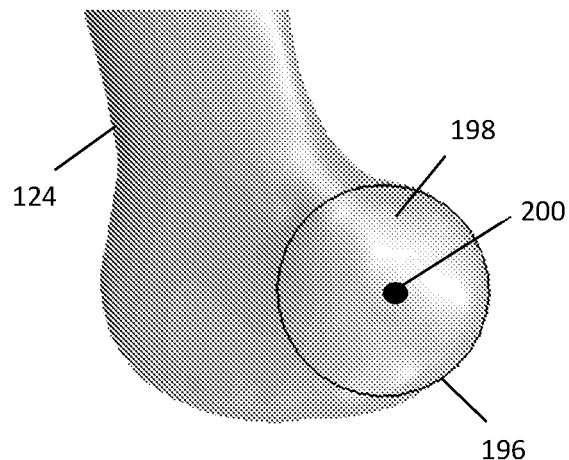
FIGS. 6A-6C depict a condylar axis about with an implant can rotate in accordance with embodiments of the invention.
Figure 6B:
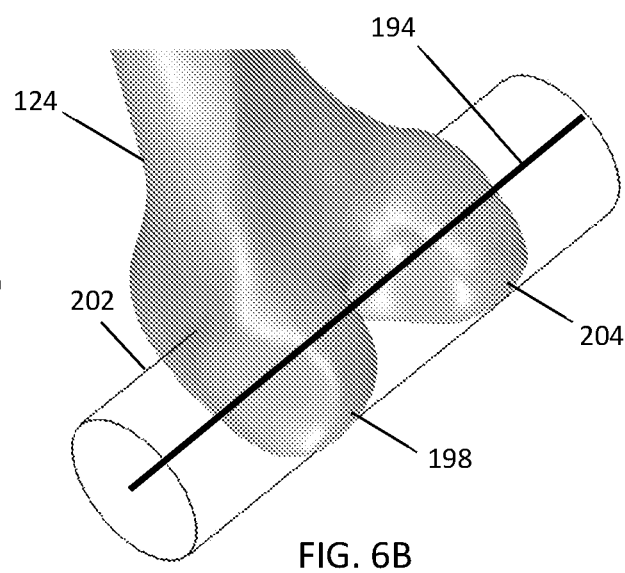
Figure 6C:
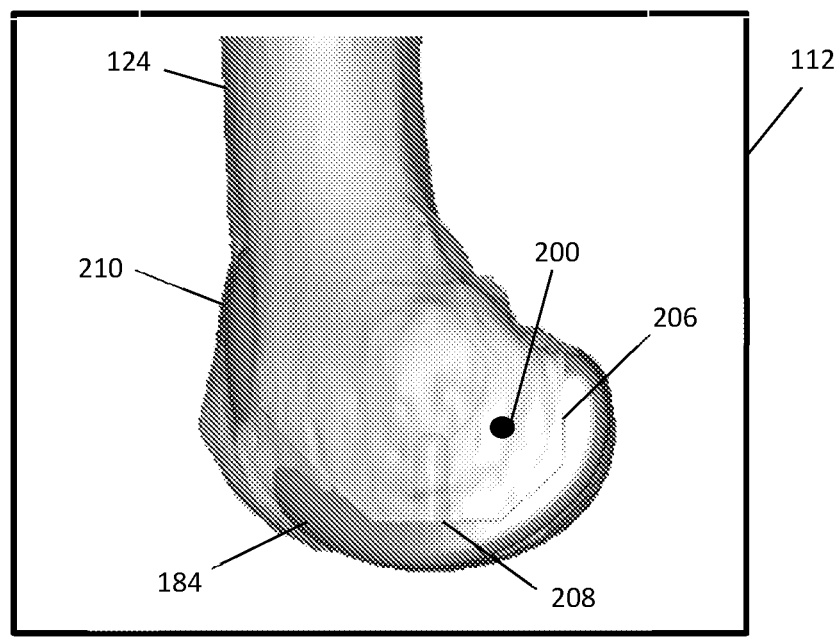

In a particular inventive embodiment, with reference to FIGS. 6A-6C, the processor determines a condylar axis 194 where any adjustment in the flexion-extension rotation direction occurs about the condylar axis 194. The condylar axis 194 may be determined by fitting one circle to a portion of the medial condyle 198, and fitting a second circle to a portion of the lateral condyle. Each circle having a center 200. An axis connecting the two centers of the circles define the condylar axis 194. In another inventive embodiment, the condylar axis 194 is determined as a center axis of a cylinder 202 traversing through the medial condyle 198 and the lateral condyle 204, where the diameter of the cylinder is best-fitted to a portion of the condyles. In another inventive embodiment, a sphere is fitted to the medial 198 and lateral condyles 204, wherein an axis connecting the center of the two spheres defines the condylar axis 194. In a specific inventive embodiment, the condylar axis 194 is determined by the following:

1. Map articular surface;
a. Re-orient bone model such that the coronal native plane is coincident with the XZ plane, the axial native plane is coincident with the XY plane, and the sagittal native plane is coincident with the YZ plane;
b. Rotate bone about global X-axis (flexing the knee) about flexion increment;
c. Locate the most-distal (−z) point in global coordinate system that has a positive x-coordinate (condyle 1 articular surface point). Locate same point in local bone coordinates.
d. Locate the most-distal (−z) point in global coordinate system that has a negative x-coordinate (condyle 2 articular surface point). Locate same point in local point coordinates:
e. Increment flexion and repeat c-d;
f. Repeat e through entire range of flexion;
2. Fit cylinder to mapped articular surface:
3. Center axis of the cylinder is the condylar axis 194.

As shown in FIG. 6C, as the implant or bone is rotated in flexion-extension about the condylar axis, the posterior resection 206 and the distal resection 208 does not substantially change because the implant is essentially rotating about the semi-circular condyles. Therefore, the user can set the anterior portion 210 of the implant such that there is no notching without affecting these resections.

Figure 7:
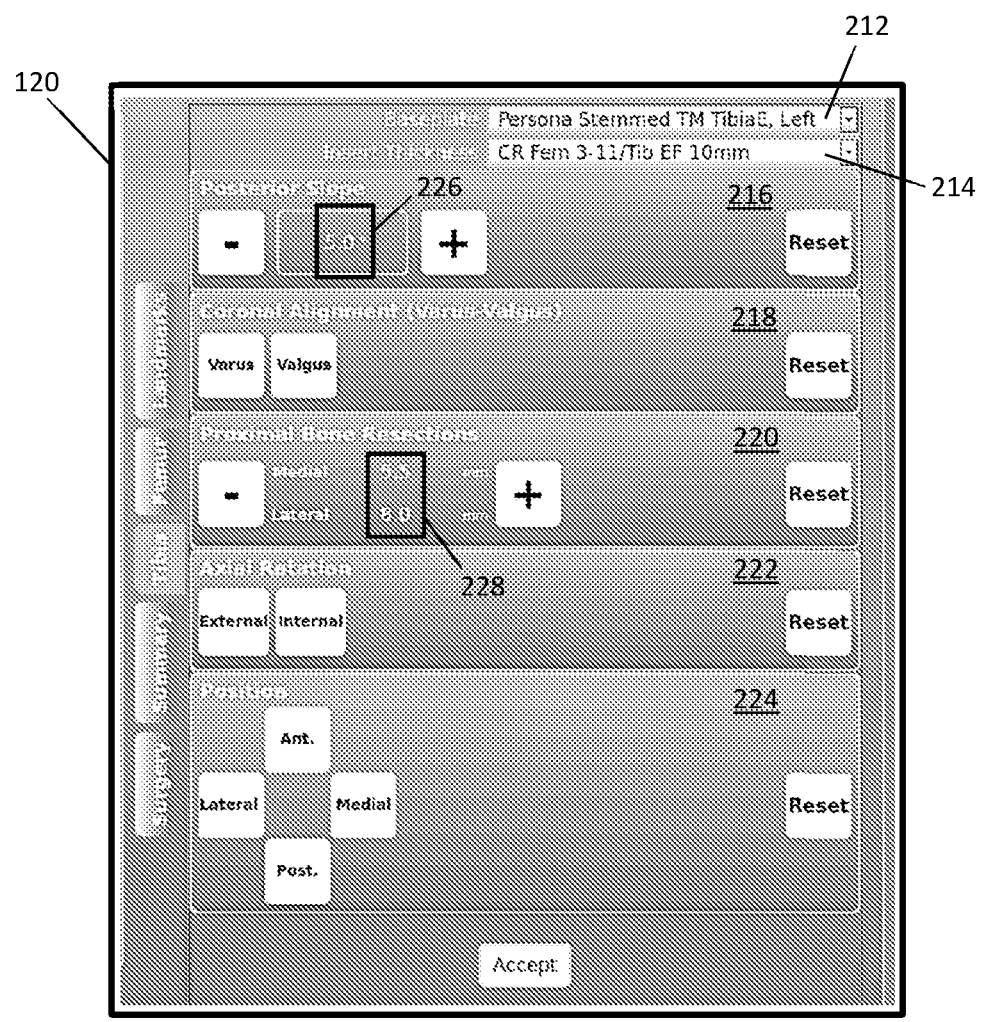
FIG. 7 depicts a tibial planning stage of the GUI in accordance with embodiments of the invention.

After the femur has been planned, the user may plan the tibia, although the user may go back and forth between the femur and tibia planning stages. The tibia component is automatically aligned to the femoral component by matching the articular surface of the tibia to the articular surface of the femoral component. As shown in FIG. 7, the user can select and re-select a tibial baseplate component using baseplate drop-down menu 212, and the user can select and re-select a tibial liner using tibial liner drop-down menu 214. The user can then adjust the posterior slop 216, coronal alignment 218, proximal bone resections 220, axial rotation 222, and translational position 224. A measured value of the tibial slope 226 is displayed and a measure value of the tibial proximal bone resections 228 is also displayed. The posterior slope is adjusted in flexion-extension about the condylar axis 194 defined on the femoral condyles as described above. The axial rotation occurs about a projection of the mechanical axis of the tibia onto the sagittal native plane 134.

Figure 8A:
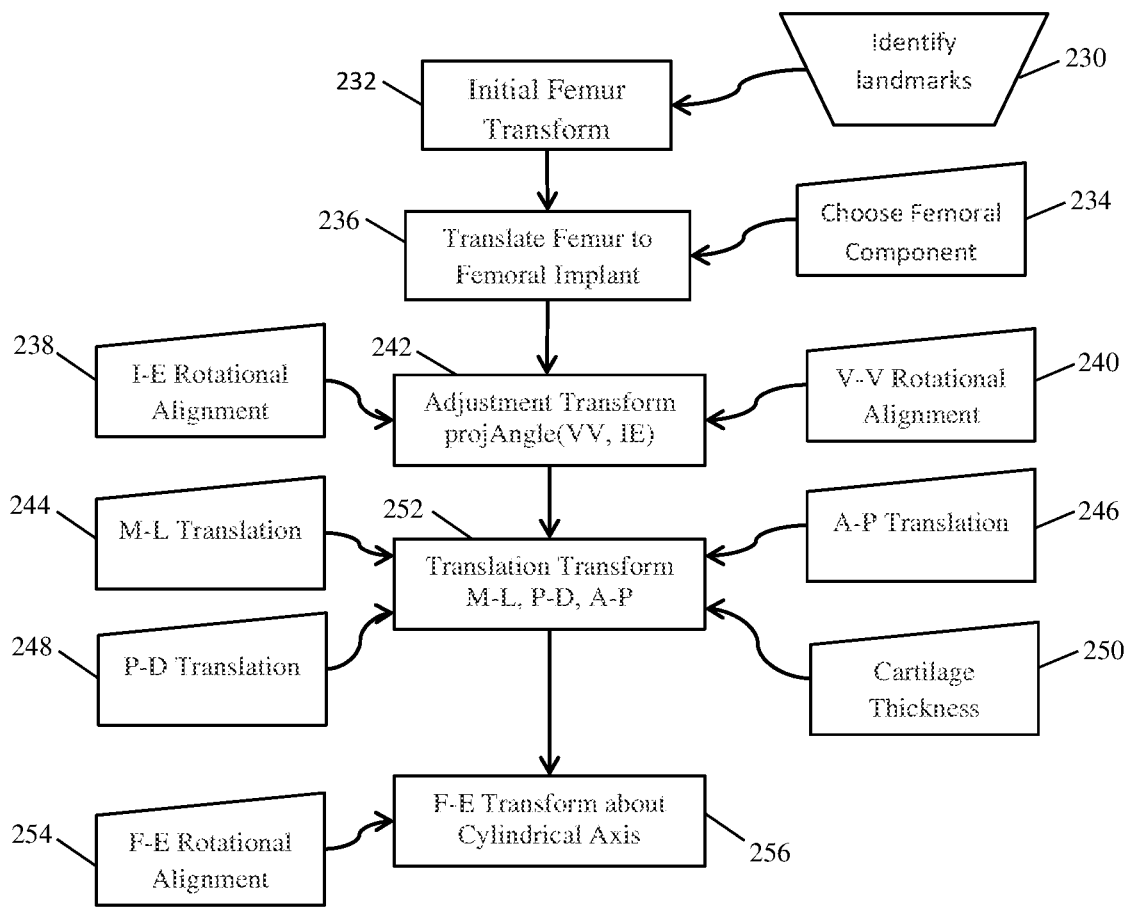
FIG. 8A illustrates a sequential order of a concatenation of femoral transforms computed by a processor in accordance with embodiments of the invention.
Figure 8B:
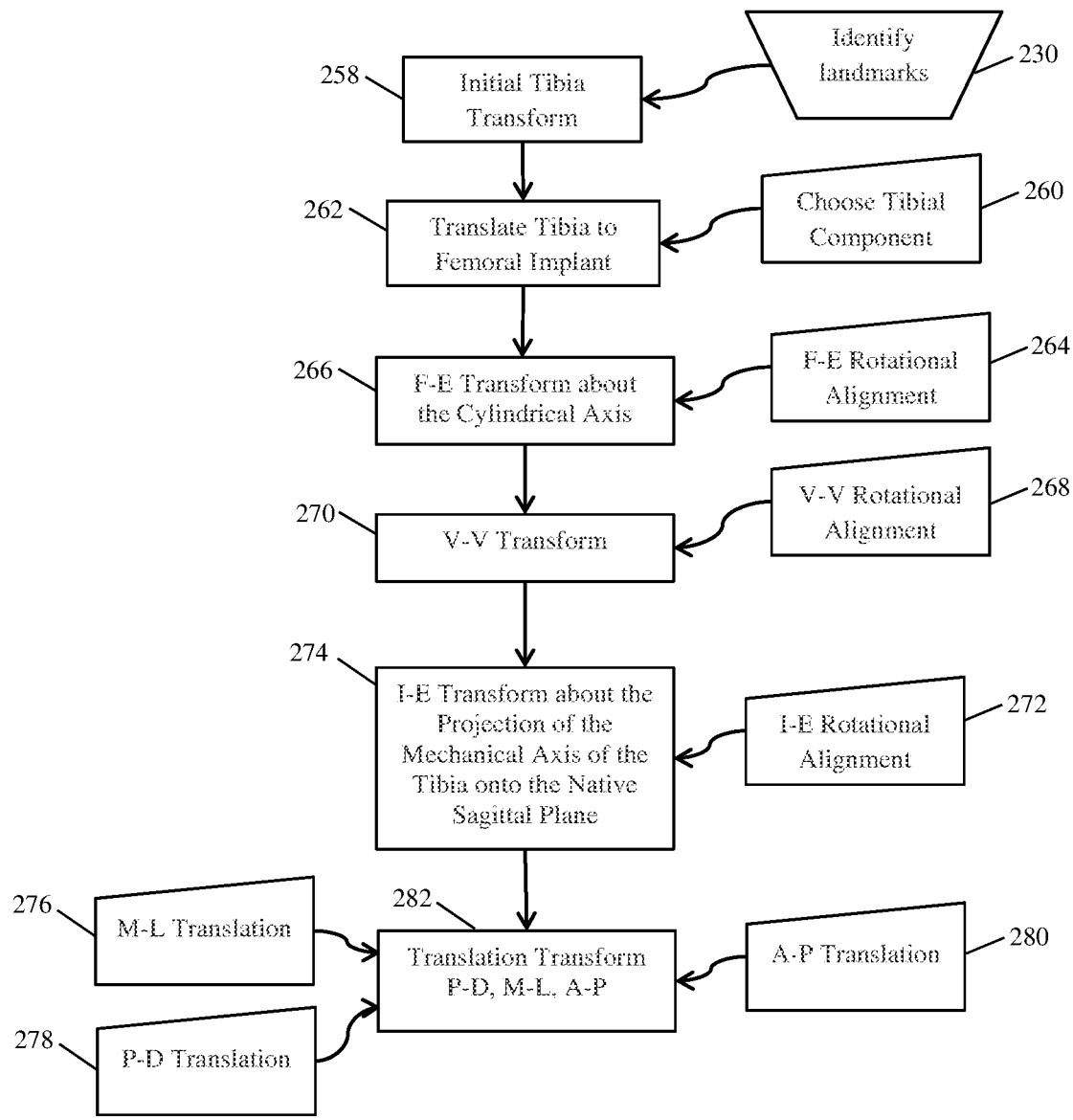
FIG. 8B illustrates a sequential order of a concatenation of tibial transforms computed by a processor in accordance with embodiments of the invention.

FIGS. 8A and 8B depict a sequential order of a concatenation of transforms that allow the user to make an adjustment in any clinical direction and/or select/re-select an alignment goal, such that the implant is re-aligned in the desired clinical direction or the re-selected alignment goal, regardless of a pre-adjusted position and orientation of the implant. This specific order of transforms is designed such that the adjustments are the inputs and the outputs. When a user makes an adjustment in a clinical direction, the model is transformed in the desired clinical direction. After the model has been transformed, the position and orientation of the implant is measured with respect to the bone, which directly correlates to adjustment made. This order is computationally fast and provides the user with an intuitive tool for aligning an implant with respect to the bone according to a clinical standard reference frame.

FIG. 8A depicts the sequential order of the concatenation of transforms computed by the processor for the femoral planning stage to intuitively align and position the femoral implant to the bone. The anatomical landmarks are determined (Block 230) and an initial femoral base transform is determined (Block 232). The second transformation is between the femoral implant component (Block 234) and the femur model (Block 236). The third transformation is an adjustment transform for femoral coronal and axial rotation (Block 242). The fourth transform is a translation transform for any adjustment in the anterior-posterior, proximal-distal, medial-lateral, and an optional account for cartilage thickness (Block 252). The final transform is an adjustment in the flexion-extension rotation direction about the condylar axis 194 (Block 256). Note, each of these transforms have default values, which allow the user to adjust any of the alignment goals or clinical directions in any sequence, however the transforms are computed in this sequential order to allow for any adjustments to occur in the desired direction regardless of the position and orientation of the implant or bone.

FIG. 8B depicts the sequence of the concatenation of transforms computed by the processor for the tibial planning stage to intuitively align and position the tibial implant to the bone. A first initial tibia transform (Block 258) from the anatomical landmarks. A second transform between the tibial component and the femoral component (Block 262). A third rotation transform in flexion-extension rotation about the condylar axis 194 (Block 266). A fourth transform in a varus-valgus alignment (Block 270). A fifth transform in internal-external rotation where the rotation occurs about the projection of the mechanical axis of the tibia to the sagittal native plane (Block 274). A final translation transform for any adjustments in a translational direction (Block 282).

The sequential order of the concatenation of transform allows the user to make adjustments to the implant or bone in an intuitive manner. Once the femur and tibial planning stages are complete, the user can review the hip-knee-ankle angles, femoral joint line alignment, tibial joint line alignment, femoral distal resections, femoral posterior resections, proximal tibial resections, and posterior slope, as well as patient information and surgical procedure information in the summary stage of the procedure. In the surgical planning stage, the user can determine which bone should be operated on first and define any parameters for a computer-assisted surgical system. The final plan is accepted by the surgeon and is written to a data transfer file (e.g., compact disc (CD), portable universal serial bus (USB)) for use with the computer-assisted surgical system. The final plan includes the final femur-to-implant transform, and the final tibia-to-implant transform to register and execute the TKA according to the plan.

In a particular inventive embodiment, if a user does not deviate from a particular planning strategy, the user may save their set of alignment goals in the planning workstation that can be applied to all surgical cases. Due to the minimal user input required by the surgeon, the saved preferences can improve pre-operative planning times.

In a specific inventive embodiment, if a user desires a native alignment, the pre-operative planning may be performed nearly automatically. The coronal native plane, axial native plane and sagittal native plane may be determined as described above. The bone wear may be accounted for by the following:

a. Varus Malalignment i. Without changing the tibia or the kinematic planes, rotate the femur in the coronal plane about an axis perpendicular to the coronal native plane and coincident with the most distal point on the lateral condyle. Rotation amount should be the arctangent of the bone wear on the lateral side divided by the distance between the two most distal points on the femur, or $$\theta = \operatorname{atan}\left(\frac{t_{wear,bone}}{d_{medial\ to\ lateral\ condyle}}\right)$$

b. Valgus Malalignment i. Without changing the tibia or the kinematic planes, rotate the femur in the coronal plane about an axis perpendicular to the coronal native plane and coincident with the most distal point on the medial condyle. Rotation amount should be the arctangent of the bone wear on the medial side divided by the distance between the two most distal points on the femur, or $$\theta = \operatorname{atan}\left(\frac{t_{wear,bone}}{d_{medial\ to\ lateral\ condyle}}\right)$$

The cartilage wear may be accounted for by the following:

a. Varus Malalignment i. Without changing the tibia or the kinematic planes, rotate the tibia in the coronal plane about an axis perpendicular to the coronal native plane and coincident with the most distal point on the lateral condyle. Rotation amount should be the arctangent of the total cartilage wear on the lateral side divided by the distance between the two most distal points on the femur, or $$\theta = \operatorname{atan}\left(\frac{t_{wear,cartilage}}{d_{medial\ to\ lateral\ condyle}}\right)$$

b. Valgus Malalignment i. Without changing the tibia or the kinematic planes, rotate the femur in the coronal plane about an axis perpendicular to the coronal native plane and coincident with the most distal point on the medial condyle. Rotation amount should be the arctangent of the total cartilage on the medial side divided by the distance between the two most distal points on the femur, or $$\theta = \operatorname{atan}\left(\frac{t_{wear,cartilage}}{d_{medial\ to\ lateral\ condyle}}\right)$$

The femoral implant size may be determined using the medial-lateral width and femoral anterior-posterior size of the femur. The femoral implant is placed on the bone model such that the articular surface of the femoral component contacts the coronal native plane and axial native plane. The two posterior condyles of the component contact the coronal native plane in exactly two points such that the component does not intersect the plane. The two distal condyles of the component contact the axial native plane in exactly two places such that the component does not intersect the plane. The femoral implant is automatically rotated in flexion-extension about the condylar axis 194, maintaining the requirements of the placement, until the most proximal part of the anterior surface of the femoral implant is on the anterior surface of the bone (no notching). The tibial component comes in linked to the femoral component at full extension and the flexion of the tibia is corrected about the femoral component flexion axis coincident with the condylar axis 194.

OTHER EMBODIMENTS

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.

The invention claimed is:

1. A computerized method for automatically placing a model of an implant relative to a model of a bone, the method comprising:
   automatically determining three orthogonal planes with respect to a virtual model of a first bone using a plurality of anatomical landmarks located on the virtual model of the first bone, wherein the three orthogonal planes comprises a coronal plane, an axial plane, and a sagittal plane of the virtual model of the first bone;
   receiving selections of:
   a first implant, and
   an alignment goal from a set of alignment goals; and
   automatically placing a virtual model of the first implant, corresponding to the selected first implant, on the virtual model of the first bone to satisfy the selected alignment goal based on a computation utilizing the selected alignment goal, the three orthogonal planes, and geometry data of the virtual model of the first implant.

2. The computerized method of claim 1 wherein the computation comprises computing a concatenation of transforms to align the virtual model of the first implant with respect to the virtual model of the first bone.

3. The computerized method of claim 2 wherein a sequential order of the concatenation of transforms includes an initial first bone transform, a first bone-to-implant transform, an alignment goal transform, a translation first bone transform, and a flexion-extension first bone rotation transform.

4. The computerized method of claim 2 wherein the portion of the geometry of the virtual model of the first implant is a plane offset by a thickness of the implant.

5. The method of claim 1 wherein the set of alignment goals a comprises varus-valgus alignment goals and axial rotational alignment goals, wherein the varus-valgus alignment goals comprise a neutral mechanical axis of the first bone and a native alignment of the first bone, and the axial rotation alignment goals comprise a parallelity to a transepicondylar axis of condyles of the first bone an angle offset from an anatomical axis of the first bone, and a native alignment of the first bone.

6. The computerized method of claim 1 further comprising receiving user adjustments of a desired change in at least one of four clinical directions, wherein each clinical direction is adjusted independently, and wherein the virtual model of the first bone with respect to the virtual model of the first implant is adjusted automatically using a calculation to satisfy the desired change.

7. The computerized method of claim 6 further comprising automatically re-placing the virtual model of the first bone with respect to the virtual model of the first implant in response to at least one of:
- an adjustment made in a desired clinical direction; or
- a re-selection of an alignment goal; and
- wherein at least one of the adjustments and the re-selection is inputted into the concatenation of transforms; and
- wherein the concatenation of transforms are computed in a sequential order to re-align the virtual model of the first implant with respect to the virtual model of first bone in the desired clinical direction or the re-selected alignment goal without affecting a pre-adjusted position and orientation of the virtual model of the first implant with respect to the virtual model of the first bone.

8. The computerized method of claim 6 further comprising receiving a user reset of an adjustment made by the user in one or more of the clinical directions to a default value.

9. The computerized method of claim 6 wherein the computer automatically determines a position and orientation of the virtual model of the first implant in six degrees of freedom with respect to the virtual model of the first bone.

10. The computerized method of claim 6 wherein the four clinical directions include a medial-lateral translation direction, a proximal-distal translation direction, an anterior-posterior translation direction, and a flexion-extension rotation direction.

11. The computerized method of claim 1 further comprising determining a condylar axis with respect to two condyles of the virtual model of the first bone, wherein the condylar axis is determined by at least one of:
- an axis connecting the center of two circles, where each circle is fitted about a portion of each condyle; or
- a transepicondylar axis of the condyles.

12. The computerized method of claim 1 wherein the determining of the three orthogonal planes comprises:
- iteratively locating three most posterior points on the virtual model of the first bone to define a coronal plane;
- iteratively locating two most distal points on the virtual model of the first bone and computing an axial plane defined as a plane normal to the coronal plane and coincident with the two most distal points; and
- locating a medial-lateral center point on the virtual model of the first bone, and computing a sagittal plane defined as a plane normal to the coronal plane, a plane normal to the axial plane, and coincident with the medial-lateral center point.

13. The computerized method of claim 1 wherein a virtual model of a second implant is automatically placed with respect to the virtual model of the first implant.

14. The computerized method claim 1 wherein the virtual model of the first bone is a virtual model of at least a portion of a femur bone.

15. A surgical planning system for performing the computerized method of claim 1 the system comprising:
- a computer comprising a processor, non-transient storage memory, and software to execute the method of claim 1.

16. The system of claim 15 further comprising a graphical user interface (GUI) comprising:
- a three-dimensional (3-D) view window, a view options window, a patient information window, an implant family window, a workflow-specific tasks window, and a limb and knee alignment measures window.

17. The computerized method of claim 1, further comprising:
- providing a graphical user interface (GUI); and
- locating the set of anatomical landmarks located on the virtual model of the first bone.

18. The computerized method of claim 1 wherein the virtual model of the first implant is selected from a library of implants.

19. The computerized method of claim 1 wherein the plurality of anatomical landmarks:
- for the first bone being a femur bone include at least one the femoral head center, most anterior point in intercondylar notch, medial epicondyle, lateral epicondyle, anterolateral trochlear ridge, anteromedial trochlear ridge, most posterior point on medial condyle, most posterior point on lateral condyle, most distal point on medial condyle, most distal point on lateral condyle, or knee center; and
- for the first bone being a tibia bone include at least one of midpoint between tibial splines, ankle center, center of medial plateau, center of lateral plateau, tibia tubercle, antero-lateral face, or antero-medial face.

\* \* \* \* \*